(12) United States Patent
Liu et al.

(10) Patent No.: US 9,131,850 B2
(45) Date of Patent: Sep. 15, 2015

(54) HIGH SPATIAL RESOLUTION OPTICAL COHERENCE TOMOGRAPHY ROTATION CATHETER

(75) Inventors: Yu Liu, Irvine, CA (US); Jiayin Liu, Irvine, CA (US)

(73) Assignee: ST. JUDE MEDICAL, INC., St. Paul, MN (US)

(*) Notice: Subject to any disclaimer, the term of this patent is extended or adjusted under 35 U.S.C. 154(b) by 496 days.

(21) Appl. No.: 13/184,655

(22) Filed: Jul. 18, 2011

(65) Prior Publication Data

US 2013/0023760 A1   Jan. 24, 2013

(51) Int. Cl.
*A61B 5/00* (2006.01)
*A61B 1/00* (2006.01)

(52) U.S. Cl.
CPC ........... *A61B 5/0084* (2013.01); *A61B 1/00167* (2013.01); *A61B 5/0066* (2013.01); *A61B 5/6852* (2013.01); *Y10T 29/49826* (2015.01)

(58) Field of Classification Search
CPC ............ A61B 1/00167; A61B 5/0066; A61B 5/0084; A61B 5/6852; Y01T 29/49826
USPC ..................... 600/473, 476, 425, 478; 65/378
See application file for complete search history.

(56) References Cited

U.S. PATENT DOCUMENTS

| | | | |
|---|---|---|---|
| 3,414,837 A * | 12/1968 | Snitzer .............................. 372/6 |
| 4,710,216 A * | 12/1987 | Harada et al. ................... 65/411 |
| 4,859,289 A * | 8/1989 | Nishimura et al. ........... 205/149 |
| 5,421,334 A * | 6/1995 | Jabba ............................. 600/466 |
| 5,463,651 A * | 10/1995 | Komachi et al. ................. 372/92 |
| 5,830,145 A * | 11/1998 | Tenhoff ......................... 600/463 |
| 6,190,353 B1 * | 2/2001 | Makower et al. .......... 604/95.01 |
| 6,222,970 B1 * | 4/2001 | Wach et al. .................... 385/115 |
| 6,891,984 B2 * | 5/2005 | Petersen et al. ................. 385/12 |
| 2002/0146202 A1 * | 10/2002 | Reed et al. ....................... 385/34 |
| 2006/0135870 A1 | 6/2006 | Webler |
| 2007/0159673 A1 * | 7/2007 | Freeman et al. ................ 359/19 |
| 2008/0073592 A1 * | 3/2008 | Panning et al. ............ 250/495.1 |
| 2009/0043191 A1 * | 2/2009 | Castella et al. ............... 600/425 |
| 2011/0021926 A1 | 1/2011 | Spencer et al. |
| 2011/0137124 A1 | 6/2011 | Milner et al. |

* cited by examiner

*Primary Examiner* — Katherine Fernandez
(74) *Attorney, Agent, or Firm* — Mattingly & Malur, PC

(57) ABSTRACT

An optical coherence tomography rotation catheter comprises a catheter body and a tubular member that rotates around a longitudinal axis in the catheter body. An optical fiber extends along an interior of the tubular member and has an optical fiber distal end. A light reflecting member is distal of the optical fiber distal end and rotates around the longitudinal axis with the tubular member. The light reflecting member includes a light reflecting surface which is spaced from and faces the optical fiber distal end and which is inclined to reflect the light from the optical fiber in a radial direction at an angle with respect to the longitudinal axis. The light reflecting member has a diameter of at most about 0.25 mm. The light reflecting surface is polished and coated with a light reflecting film.

14 Claims, 6 Drawing Sheets

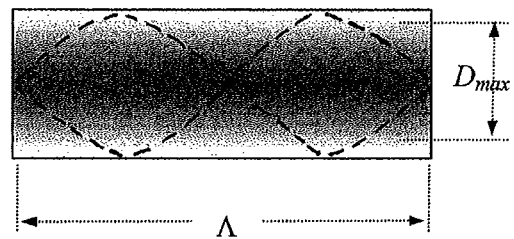
FIG. 5
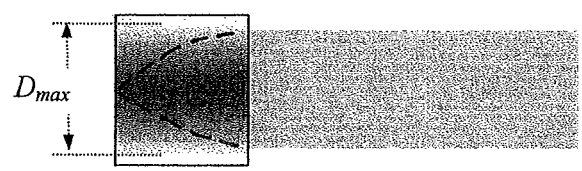
FIG. 6
| LBE (mm) | um | n0 | NA | n1 | NA2 | D(um) | delta | Diameter (um) | f (mm) | experiment (mm) |
|---|---|---|---|---|---|---|---|---|---|---|
| 0 | 8.5 | 1.467 | 0.09 | 1.487 | 0.29 | 100 | 0.019017 | 39.96 | 0.38 | 0.35 |
| 0.65 | | | | | | | | 87.00 | 1.78 | 1.5 |
FIG. 7

HIGH SPATIAL RESOLUTION OPTICAL COHERENCE TOMOGRAPHY ROTATION CATHETER

BACKGROUND OF THE INVENTION

The present invention relates generally to scanning imaging devices and, more specifically, to a high spatial resolution rotation catheter for use in optical coherence tomography or the like.

When light reflected from samples interferes with a reference beam, the frequencies of the interfering signals reveal the depth where the light is reflected. This technique has been used in imaging, known as Optical Coherence Tomography (OCT). OCT is an optical signal acquisition and processing method allowing extremely high-quality, micrometer-resolution, three-dimensional images from within optical scattering media (e.g., biological tissue) to be obtained. Scanning imaging probes are used in OCT and other interferometric imaging and ranging systems, as well as for delivery of other imaging modalities or therapeutic optical sources. See, e.g., U.S. Pat. No. 6,891,984, which is incorporated herein by reference in its entirety.

Typical fiber rotation probes for OCT imaging include fiber GRIN (Gradient-Index) lenses and micro-prisms. The disadvantage of using a micro-prism is that the emitting surface is curved. This curved surface acts as a cylinder lens that degrades the laser beam quality. The focal spot is in an elliptical shape rather than a circular shape. Polishing the curved surface of the fiber into a flat surface would solve this problem, but the mechanical processing could be very difficult. The high cost of the mechanical processing is another issue, since the fiber size micro-prisms (e.g., about 0.125 mm in diameter) that are attached to the fiber GRIN lenses are not suitable for mass production. The polished micro-prisms also require a clear tubing to form a kind of air bag to protect the polished surface in order to achieve a full internal reflection. Another disadvantage is the need for a fluid occupying the space between the prism and the inner sheath of the catheter in order to balance optical aberrations due to cylindrical lens effect. See, e.g., U.S. Patent Application Publication No. 2011/0137124. As such, the distal end of the stationary part of the catheter must be open, making it vulnerable to dust contamination.

Alternatively, fiber rotation probes for OCT imaging using fiber GRIN lenses and micro-mirrors are also a popular design. One benefit of using a micro-mirror instead of a micro-prism is that there is no cylinder lens effect. The high cost of processing remains an issue, however, since the small size micro-mirrors are not commercially available and the processing cost for polishing and coating each micro-mirror to provide a highly reflective surface is very high. Currently, micro-mirrors are about 0.5 mm in diameter. Heretofore, micro-mirrors having a diameter of at most about 0.25 mm have not been made successfully.

BRIEF SUMMARY OF THE INVENTION

Exemplary embodiments of the invention provide apparatuses and methods for a high spatial resolution rotation catheter for use in optical coherence tomography or the like. The rotation catheter has a rotary part which rotates with respect to a stationary part. At the distal end of the rotary part is an optical tip where a fiber probe is disposed. The fiber probe includes an angled micro-mirror spaced from a GRIN lens. The micro-mirror has an inclined surface at an angle of typically about 35°-45° to reflect the light from the GRIN lens in the longitudinal direction to a lateral or radial direction outwardly from the longitudinal axis of the rotary part. The rotation of the rotary part rotates the reflected light beam in the circumferential direction. The use of the micro-mirror minimizes optical aberration (no aberration theoretically). As a result, no fluid is required to balance optical aberrations and thus the distal end of the stationary part can be sealed to prevent blood from blocking the optical window of the fiber probe and prevent any dust from contaminating the blood. Furthermore, the invention employs a process to manufacture a plurality of micro-mirrors in a bundle that provides a larger effective lateral dimension. The bundle has at least five longitudinal members to be polished and coated. The bundle preferably has tens of longitudinal members and more preferably has over 100 longitudinal members. This manufacturing process makes it possible to make a micro-mirror having a diameter of at most about 0.25 mm and an inclined light reflecting surface at a constant angle with high reflectivity.

In accordance with an aspect of the present invention, an optical coherence tomography (OCT) rotation catheter comprises: a catheter body; a tubular member disposed in the catheter body, the tubular member having a hollow interior extending between a proximal end and a distal end, a longitudinal axis extending in a longitudinal direction between the distal end and the proximal end, the tubular member being rotatable around the longitudinal axis; an optical fiber extending along the hollow interior of the tubular member and having an optical fiber distal end at a location near the distal end of the tubular member to direct light through the optical fiber distal end toward the distal end of the tubular member; and a light reflecting member which is disposed in the hollow interior of the tubular member and distal of the optical fiber distal end and which is configured to rotate around the longitudinal axis with the tubular member, the light reflecting member including a light reflecting surface which is spaced from and faces the optical fiber distal end and which is inclined to reflect the light from the optical fiber in a radial direction at an angle with respect to the longitudinal axis, the reflected light rotating in a circumferential direction due to rotation of the light reflecting member around the longitudinal axis. The light reflecting member has a diameter of at most about 0.25 mm, and the light reflecting surface is polished and coated with a light reflecting film.

In some embodiments, the light reflecting member is made of a material selected from the group consisting of metallic materials, fiber materials, and glass materials. In one preferred embodiment, the material is stainless steel. The light reflecting film comprises a material selected from the group consisting of aluminum, silver, gold, and dielectric coating materials. The light reflecting member and the optical fiber distal end are attached to the tubular member to rotate with the tubular member around the longitudinal axis; and the tubular member is rotatable with respect to the catheter body, the catheter body has a distal end which is distal of the distal end of the tubular member, and the distal end of the catheter body is sealed. The tubular member and the catheter are optically transparent at least in a region near the light reflecting member to allow the reflected light from the light reflecting surface to pass therethrough.

In specific embodiments, the OCT rotation catheter further includes a beam expander having a first end coupled to the distal end of the optical fiber and having a second end, the beam expander permitting a light beam emitting from a fiber core of the optical fiber to pass from the first end to the second end and to expand from the first end to a larger beam size at the second end. A gradient-index fiber lens is coupled to the second end of the beam expander to receive the light beam from the beam expander and focus the light beam. The gradient-index fiber lens is proximal of the light reflecting member and spaced from the light reflecting surface. The optical fiber is a single mode fiber, and the beam expander comprises a no core fiber or a step-index multimode fiber. The gradient-index fiber lens has a core surrounded by a glass cladding or air, the core having a refractive index that varies with a radial distance from an axis of the gradient-index fiber lens, decreasing radially outwardly toward the cladding, and the core of the gradient-index fiber lens has a diameter which is not smaller than an outer diameter of the beam expander. The gradient-index fiber lens has a refractive index that varies with a radial distance from an axis of the gradient-index fiber lens, decreasing radially outwardly, and the gradient-index fiber lens has a diameter which is not smaller than an outer diameter of the beam expander.

In some embodiments, the stationary shaft tubular member is optically transparent at least in a region near the light reflecting member to allow the reflected light from the light reflecting surface to pass therethrough. The tubular member is rotatable with respect to the catheter body, and a clearance of less than about 0.25 mm is provided between the outer surface of the tubular member and the inner surface of the catheter body.

Another aspect of the invention is directed to a method of forming an optical coherence tomography (OCT) rotation catheter. The method comprises: placing a tubular member in a catheter body, the tubular member having a hollow interior extending between a proximal end and a distal end, a longitudinal axis extending in a longitudinal direction between the distal end and the proximal end, the tubular member being rotatable around the longitudinal axis; providing an optical fiber extending along the hollow interior of the tubular member and having an optical fiber distal end at a location near the distal end of the tubular member to direct light through the optical fiber distal end toward the distal end of the tubular member; forming a light reflecting member which has a diameter of at most about 0.25 mm; and positioning the light reflecting member in the hollow interior of the tubular member and distal of the optical fiber distal end and which is configured to rotate around the longitudinal axis with the tubular member, the light reflecting member including a light reflecting surface which is spaced from and faces the optical fiber distal end and which is inclined to reflect the light from the optical fiber in a radial direction at an angle with respect to the longitudinal axis, the reflected light rotating in a circumferential direction due to rotation of the light reflecting member around the longitudinal axis. Forming the light reflecting member comprises forming a bundle of at least five longitudinal members having surfaces exposed at an end of the bundle, the longitudinal members; polishing collectively the exposed surfaces of the longitudinal members at the end of the bundle; coating the polished surfaces of the longitudinal members with a light reflecting film; and separating the bundle to provide each longitudinal member as a light reflecting member having the coated surface as a light reflecting surface.

In some embodiments, the method further comprises attaching the light reflecting member and the optical fiber distal end to the tubular member to rotate with the tubular member around the longitudinal axis with respect to the catheter body, and sealing a distal end of the catheter body which is distal of the distal end of the tubular member.

Another aspect of this invention is directed to a method of providing a light reflecting member having a light reflecting surface. The method comprises: forming a bundle of at least five longitudinal members having surfaces exposed at an end of the bundle, the longitudinal members; polishing collectively the exposed surfaces of the longitudinal members at the end of the bundle; coating the polished surfaces of the longitudinal members with a light reflecting film; and separating the bundle to provide each longitudinal member as a light reflecting member having the coated surface as a light reflecting surface.

In some embodiments, the longitudinal members each have a diameter of at most about 0.25 mm. The bundle has at least 100 longitudinal members.

These and other features and advantages of the present invention will become apparent to those of ordinary skill in the art in view of the following detailed description of the specific embodiments.

BRIEF DESCRIPTION OF THE DRAWINGS

FIG. 5 illustrates an optical schematic of light rays propagation along a GRIN fiber, showing periodical beam focusing.

FIG. 6 illustrates an optical schematic of light rays propagating along a GRIN fiber, showing that a quarter period length could collimate a beam into a parallel beam if the diffraction could be ignored.

FIG. 7 is a table showing experimental results of the focal length for a GRIN fiber spliced onto a single mode fiber and the focal length for a fiber GRIN lens having a no core fiber as a beam expander spliced between the GRIN fiber and a single mode fiber.

DETAILED DESCRIPTION OF THE INVENTION

Figure 1A:
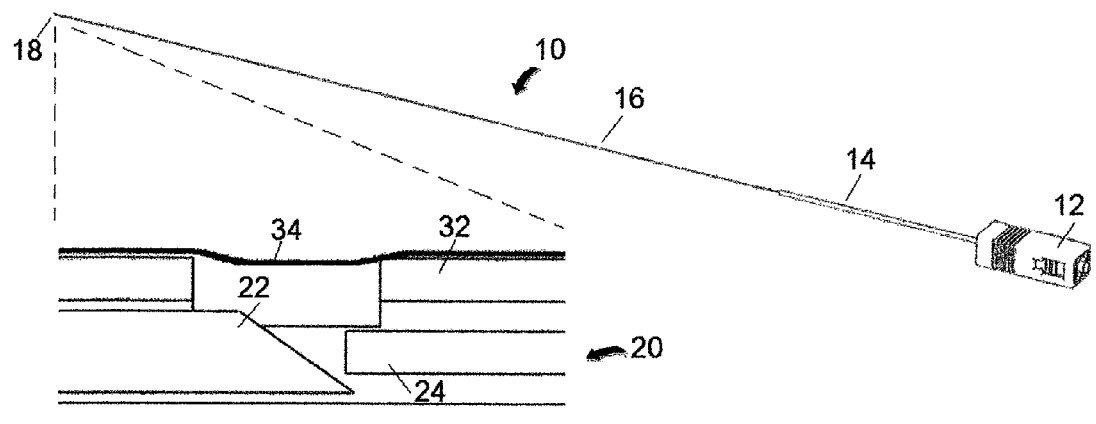
FIG. 1A is a schematic view of the rotary part of a rotation catheter according to an embodiment of the present invention.

In the following detailed description of the invention, reference is made to the accompanying drawings which form a part of the disclosure, and in which are shown by way of illustration, and not of limitation, exemplary embodiments by which the invention may be practiced. In the drawings, like numerals describe substantially similar components throughout the several views. Further, it should be noted that while the detailed description provides various exemplary embodiments, as described below and as illustrated in the drawings, the present invention is not limited to the embodiments described and illustrated herein, but can extend to other embodiments, as would be known or as would become known to those skilled in the art. Reference in the specification to "one embodiment," "this embodiment," or "these embodiments" means that a particular feature, structure, or characteristic described in connection with the embodiment is included in at least one embodiment of the invention, and the appearances of these phrases in various places in the specification are not necessarily all referring to the same embodiment. Additionally, in the following detailed description, numerous specific details are set forth in order to provide a thorough understanding of the present invention. However, it will be apparent to one of ordinary skill in the art that these specific details may not all be needed to practice the present invention. In other circumstances, well-known structures, materials, circuits, processes and interfaces have not been described in detail, and/or may be illustrated in block diagram form, so as to not unnecessarily obscure the present invention.

In the following description, relative orientation and placement terminology, such as the terms horizontal, vertical, left, right, top and bottom, is used. It will be appreciated that these terms refer to relative directions and placement in a two dimensional layout with respect to a given orientation of the layout. For a different orientation of the layout, different relative orientation and placement terms may be used to describe the same objects or operations.

Exemplary embodiments of the invention, as will be described in greater detail below, provide apparatuses and methods for a high spatial resolution rotation catheter for use in optical coherence tomography or the like.

1. Rotation Catheter Assembly

FIG. 1A is a schematic view of the rotary part of a rotation catheter according to an embodiment of the present invention. The rotary part 10 has a proximal end coupled to a fiber connector 12. The proximal portion of the rotary part 10 is a tubing 14 that is preferably made of straight and flexible material such as Nitinol or the like. The distal portion of the rotary part 10 is a torque coil 16. The proximal tubing 14 may be glued, laser welded, or otherwise affixed to the fiber connector 12 and the torque coil 16. At the distal end of the rotary part 10 is an optical tip 18 where a fiber probe 20 is disposed. The fiber probe 20 includes an angled micro-mirror 22 spaced from a GRIN lens 24. As described in greater detail below, the GRIN lens 24 is used to focus a light beam emitted by an optical fiber extending from the fiber connector 12, with the help of a beam expander between the terminal end of the optical fiber and the GRIN lens 24, to achieve a substantially longer focal length than that of a GRIN lens alone (e.g., a focal length of about 1.8-2.0 mm). The micro-mirror 22 has an inclined surface at an angle of typically about 35°-45° to reflect the light from the GRIN lens 24 in the longitudinal direction to a lateral or radial direction outwardly from the longitudinal axis of the rotary part 10. The rotation of the rotary part 10 rotates the reflected light beam in the circumferential direction. In the specific embodiment shown in FIG. 1A, the optical tip 18 has a stainless steel rotary tubing 32 with a clear tubing portion 34 to provide an optical window that is optically transparent and allows the light beam reflected from the micro-mirror 22 to pass therethrough to a target tissue and back to single mode fiber via the micro-mirror 22.

Figure 1B:
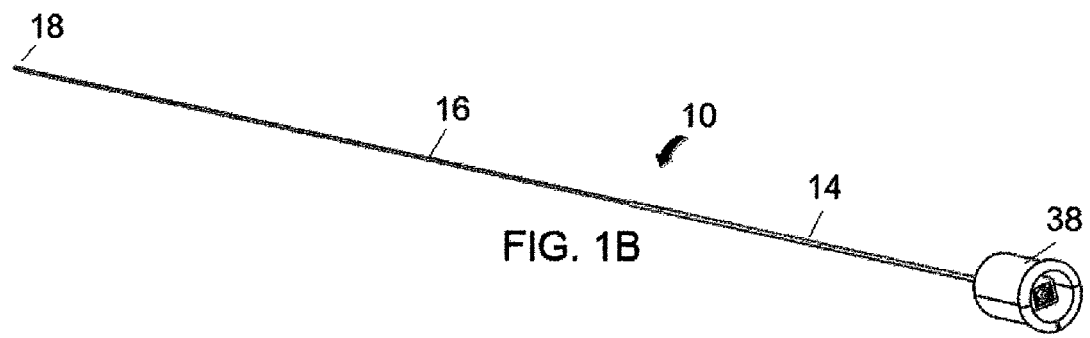
FIG. 1B is another schematic view of the rotary part of the rotation catheter of FIG. 1A.

FIG. 1B is another schematic view of the rotary part 10 of the rotation catheter of FIG. 1A. The fiber connector 12 is mounted into a rotary connector housing 38. The rotary housing 38 is a component of the rotary part 10 that rotates around the longitudinal axis.

Figure 1C:
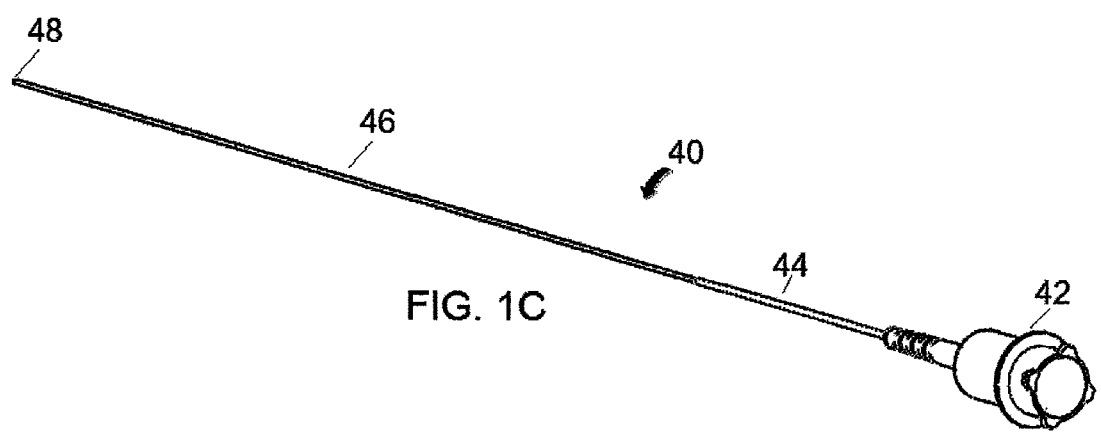
FIG. 1C is a schematic view of a stationary part of the rotation catheter according to an embodiment of the present invention.

FIG. 1C is a schematic view of a stationary part of the rotation catheter according to an embodiment of the present invention. The stationary shaft 40 includes a stationary connector housing 42, a large diameter proximal tubing 44, and a long distal tubing 46. The distal tubing 46 is preferably optically transparent to allow light to pass therethrough, and may be made of FEP (fluorinated ethylene propylene) or the like. The rotary part 10 is mounted inside the stationary part 40, with the rotary connector housing 38 inside the stationary connector housing 42, the rotary part proximal tubing 14 inside the stationary part proximal tubing 44, and the torque coil 16 inside the transparent distal tubing 46. Generally, small clearance (e.g., less than about 0.25 mm) is provided between the corresponding components of the rotary part 10 and the stationary part 40 to allow the rotary part 10 to rotate around the longitudinal axis with respect to the stationary part 40. A distal end 48 of the stationary part 40 is located near and is distal of the optical tip 18 of the rotary part 10, and is preferably sealed to prevent blood from blocking the optical window of the clear tubing portion 34 and prevent any dust from contaminating the blood. There is about 25 mm clearance or less between the sealed distal end 48 of the stationary part 40 and the distal tip 18 of the rotary part 10.

Figure 1D:
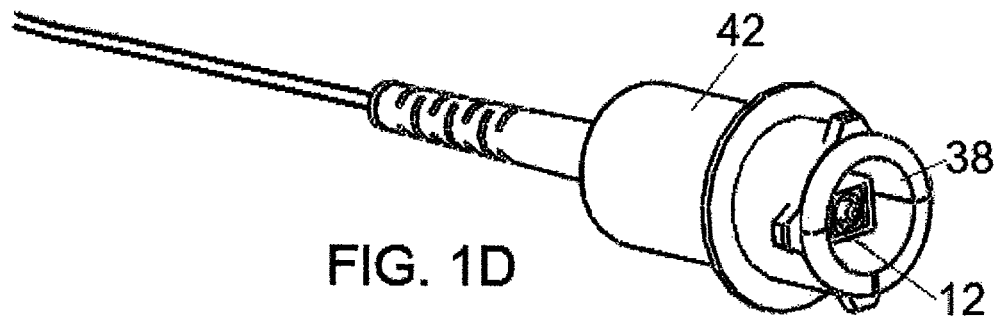
FIG. 1D is a perspective view of a fiber connector assembly of the rotation catheter.

FIG. 1D is a perspective view of a fiber connector assembly of the rotation catheter. The rotary part 10 is inserted inside the stationary part 40, as mentioned above. The rotary connector housing 38 is inside the stationary connector housing 42. The rotary connector housing 38 is attached to the fiber connector 12 and they rotate together. There is a small gap between the rotary connector housing 38 and the stationary connector housing 42.

Figure 2A:
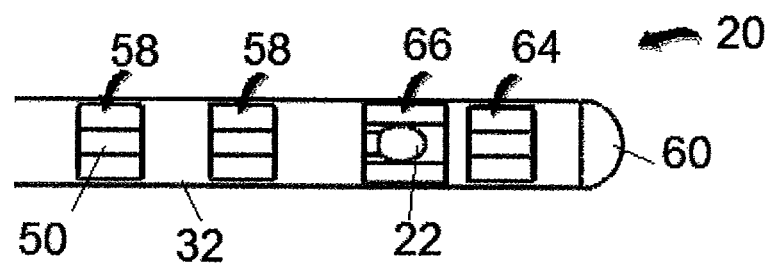
FIG. 2A is a schematic elevational view of a fiber probe as a component of the rotation catheter according to an embodiment of the invention.
Figure 2B:
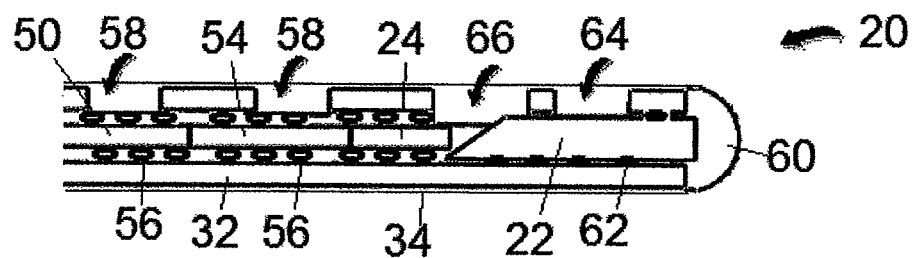
FIG. 2B is a partial cross-sectional view of the fiber probe of FIG. 2A.

FIG. 2A is a schematic elevational view of a fiber probe as a component of the rotation catheter according to an embodiment of the invention. FIG. 2B is a partial cross-sectional view of the fiber probe of FIG. 2A. As discussed above in connection with FIG. 1A, the fiber probe 20 is disposed at the optical tip 18 of the rotary part 10. The GRIN lens 24 is used to focus a light beam emitted by an optical fiber 50 extending from the fiber connector 12, with the help of a beam expander 54 between the terminal end of the optical fiber 50 and the GRIN lens 24, to achieve a substantial focal length toward the micro-mirror 22. In general, the GRIN lens 24 has a refractive index that varies with a radial distance from an axis of the GRIN lens 24, decreasing radially outwardly, and has a diameter which is not smaller than an outer diameter of the beam expander 54. In the embodiment shown, the GRIN lens 24 has a core surrounded by a glass cladding or air, and the core has a refractive index that varies with a radial distance from an axis of the GRIN lens 24, decreasing radially outwardly toward the cladding. The core of the GRIN lens 24 has a diameter which is not smaller than an outer diameter of the beam expander 54. The beam expander 54 has a first end coupled to the distal end of the optical fiber 50 and has a second end, and it permits a light beam emitting from a fiber core of the optical fiber 50 to pass from the first end to the second end and to expand from the first end to a larger beam size at the second end. In specific embodiments, the beam expander 54 comprises a no core fiber or a step-index multimode fiber (SI-MMF). In FIG. 2B, the micro-mirror 22 has a 35°-45° inclined surface to reflect the light from the GRIN lens 24 in the longitudinal direction to a lateral or radial direction outwardly from the longitudinal axis of the rotary part 10. The rotation of the rotary part 10 rotates the reflected light beam in the circumferential direction. The optical tip 18 preferably has a rounded distal end 60 to reduce rotary friction. Additional details of making and configuring the fiber probe 20 are described below.

The optical fiber 50 is attached to the distal end portion of the torque coil 16 by adhesive 56, laser welding, or the like. One or more openings or windows 58 are used to apply the adhesive 56. The components of the fiber probe 20 (micro-mirror 22 and GRIN lens 24) are attached to the stainless steel tubing 32 by adhesive 62 or the like. One or more openings or windows 64 are used to apply the adhesive 62. One optical window 66 is provided for emitting the light beam reflected by the micro-mirror 22. The rotary tubing 32 has a length of about 5 mm in a specific embodiment and may be made of some other metal or material that is sufficiently strong to support the components of the fiber probe 20. To provide the clear tubing portion 34 to allow the light beam reflected from the micro-mirror 22 to pass therethrough, one way is to use a piece of thin clear heat shrink tubing over all openings or windows 58, 64, 66.

2. Micro-Mirror

Figure 3A:
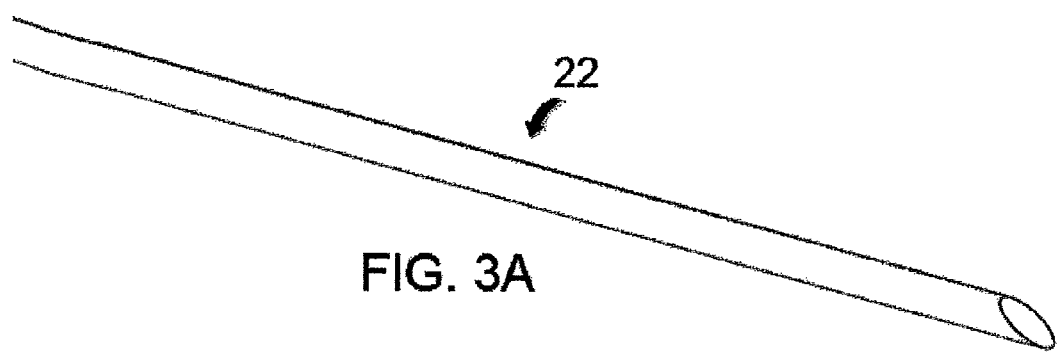
FIG. 3A is an elevational view of an angled micro-mirror as a component of the fiber probe of FIG. 2A.

FIG. 3A is an elevational view of an angled micro-mirror as a component of the fiber probe of FIG. 2A. The micro-mirror 22 is a light reflecting member which can be made of a variety of materials such as a metallic material, a fiber material, or a glass material. In one preferred embodiment, the material is stainless steel. The inclined light reflecting surface is polished and coated with a light reflecting film, which is preferably highly reflective. Examples include aluminum, silver, and gold. Possible alternative reflective coatings include dielectric coatings such as magnesium fluoride, calcium fluoride, aluminum oxide, silicon dioxide, and titanium dioxide. The micro-mirror 22 typically has an average length of about 0.5-1 mm and a diameter of about 0.1-0.2 mm. The average length is the length along the longitudinal axis; the actual length varies in the radial direction from the longitudinal axis because the light reflecting surface is inclined. The longitudinal dimension of the micro-mirror 22 is substantially larger than the lateral dimension (e.g., a ratio of about 2.5-10).

Figure 3B:
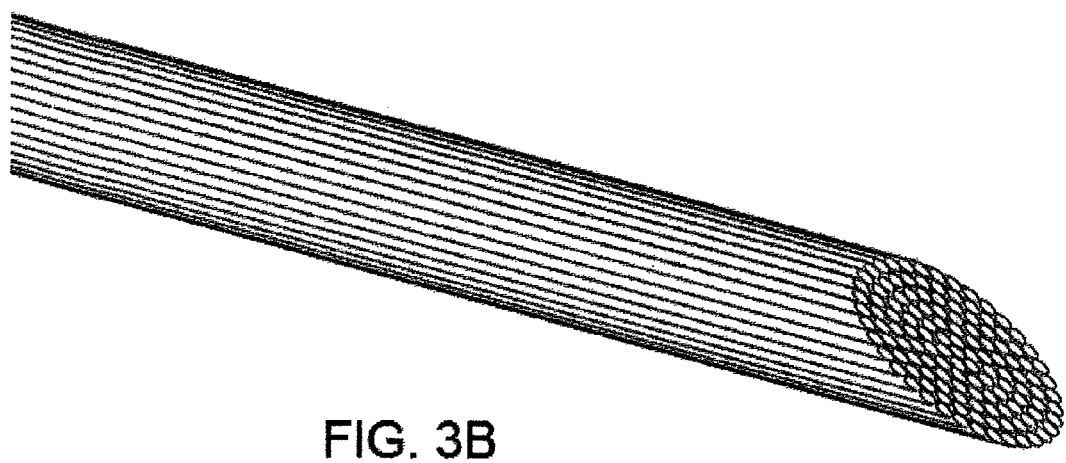
FIG. 3B is an elevational view of a bundle of micro-mirrors which are polished and coated with a high reflectivity film in a manufacturing process according to an embodiment of the invention.

FIG. 3B is an elevational view of a bundle of micro-mirrors which are polished and coated with a high reflectivity film in a manufacturing process according to an embodiment of the invention. Due to the small size of a micro-mirror 22 (less than about 0.25 mm in diameter and typically about 0.1-0.2 mm in diameter) and the small lateral dimension with respect to the longitudinal dimension, it is difficult to manufacture an individual micro-mirror by polishing and coating. The solution according to an aspect of this invention is to manufacture a plurality of micro-mirrors in a bundle that provides a larger effective lateral dimension. It is critical that a bundle has at least five longitudinal or cylindrical members to be polished and coated. The bundle preferably has tens of longitudinal members and more preferably has over 100 longitudinal members. The longitudinal members are typically about 25 mm in length and are cut to an average length of about 0.5-1 mm at the processed bundle end after the polishing and coating at the bundle end are completed.

Figure 4:
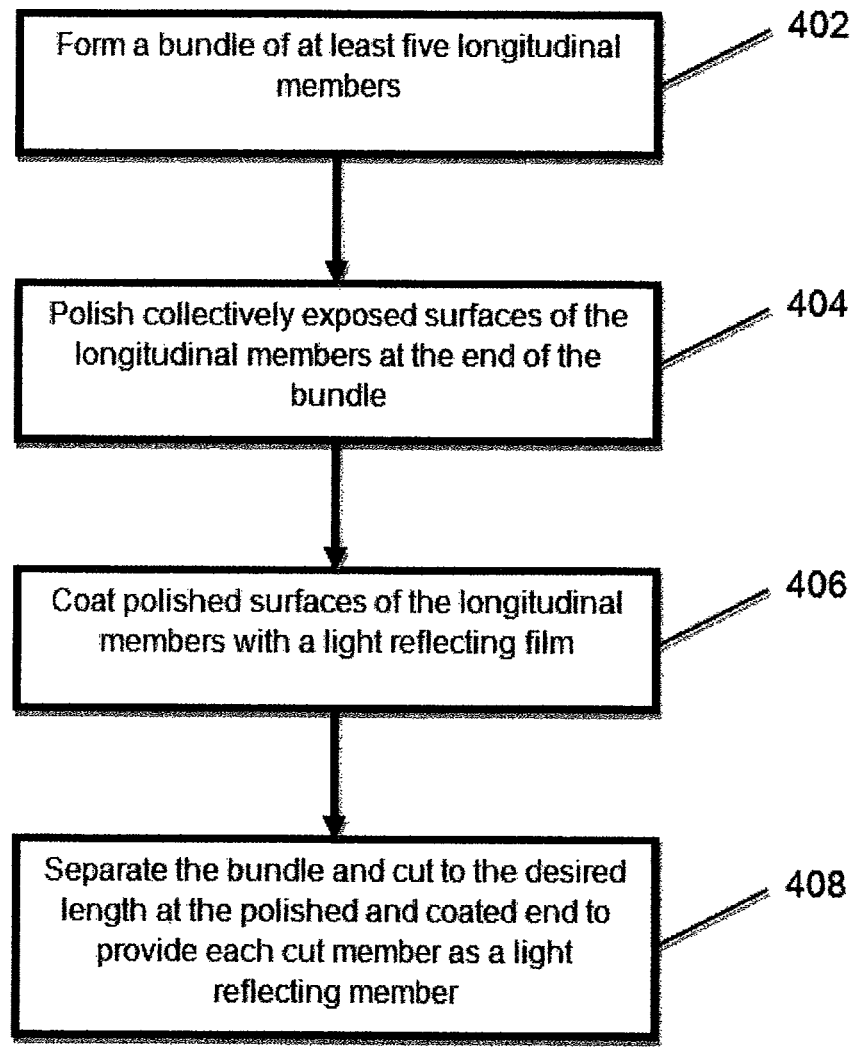
FIG. 4 is an example of a flow diagram illustrating a process of manufacturing micro-mirrors according to an embodiment of the invention.

FIG. 4 is an example of a flow diagram illustrating a process of manufacturing micro-mirrors according to an embodiment of the invention. In step 402, a bundle of at least five longitudinal members is formed. The longitudinal members having surfaces exposed at an end of the bundle. Examples of longitudinal members include stainless steel wires, glass rods, and polyimide fibers. To form the bundle, the longitudinal members can be wrapped using a heat shrink tubing or the like. In addition, the longitudinal members may be temporarily glued or otherwise affixed together to prevent relative movement to ensure effective polishing and coating to produce proper angled reflective surfaces on the micro-mirrors. Step 404 polishes collectively the exposed surfaces of the longitudinal members at the end of the bundle. The polishing is done at an angle to the longitudinal axis of the bundle to create a common angled surface on each of the longitudinal members. The polishing may be performed with solid sand papers and/or liquid polish. In specific embodiments, the polishing is done initially with solid sand papers of different sizes ranging from about 40 μm to about 1 μm, followed by liquid polish with particle size of about 0.1 μm or smaller. In step 406, the polished surfaces of the longitudinal members are coated with a light reflecting film. In step 408, the bundle is separated and cut to the desired length at the polished and coated end to provide each cut longitudinal member as a light reflecting member having the coated surface as a light reflecting surface.

The inventors have utilize the method using a bundle of 130 stainless steel wires to make micro-mirrors by polishing and coating. The diameter of a micro-mirror is about 0.1-0.2 mm and the average length is about 0.5-1 mm. The bundle diameter is about 3-4 mm for a bundle of 130 longitudinal members. The number of longitudinal members per bundle can be increased to a few hundreds or thousands. For a bundle of 10,000 wires, the overall bundle size is about 25 mm in diameter. This technique is effective and dramatically reduces the cost of making the micro-mirrors. The reflectivity of the silver-coated micro-mirrors is about 96% at 1310 nm wavelength band for the bundle of 130 micro-mirrors, corresponding to 0.35 dB loss for a round-trip. This reflectivity can be improved to about 98-99% with gold coating. The manufacturing cost per micro-mirror is substantially lower than conventional methods. The manufacturing process is commercially viable due to the low cost. The silver-coated stainless steel micro-mirrors are used to fabricate OCT rotary probes to achieve very good imaging with improved spatial resolution because the optical aberration, especially the cylinder lens effect, has been minimized.

In assembling the OCT rotary probe 20 for the OCT rotation catheter, the fiber GRIN lens 24 and the micro-mirror 22 are sufficiently small in size so that they can be assembled within the rotary tubing 32. The OCT rotation catheter does not require the use of flush or lubricant, so that no dust comes out into the blood stream of the patient, thereby ensuring safety. The rotary probe 20 may be re-useable since it is isolated from the blood stream of the patient. Another feature of the rotary probe 20 is that the GRIN lens 24 and beam expander 54 are configured with the optical fiber 50 to produce a long focal length, as described below.

3. Gradient-Index (GRIN) Lens

FIG. 5 illustrates an optical schematic of light rays propagation along a GRIN fiber, showing periodical beam focusing. FIG. 6 illustrates an optical schematic of light rays propagating along a GRIN fiber, showing that a quarter or three quarters period length can collimate a beam into a parallel beam if the diffraction can be ignored. If the incident beam is a point size, the $$\left(\frac{k}{2} + \frac{1}{4}\right)\Lambda$$

length is theoretically the best length for the GRIN lens to collimate a beam, where k=0,1,2, ... Λ is the period of the GRIN fiber. Because an actual incident beam has a significant beam diameter rather than a point source, the actual length to use for the fiber GRIN lens will be shorter than the quarter period. It is worth to note that since the period (Λ) is related to the incident angle; a large number k will significantly degrade the performance of the focusing. When the incident beam is close in size to the diameter of GRIN fibers, simulations and experiments show that the length of the GRIN fiber to use will be much shorter than the quarter period length (k=0).

The index profile of a GRIN fiber is usually expressed as $$n(\rho) = \begin{cases} n_{1,grin}\sqrt{1-2(\rho/a)^2\Delta} & (\rho \le a) \\ n_{2,grin} & (\rho > a) \end{cases} \quad (1)$$

where a, $n_{1,grin}$ and $n_{2,grin}$ are the radius of the fiber, and indexes of core and cladding, respectively. $0 \le \rho \le a$ represents the radius of light trace. The parameter $\Delta$ is expressed as $$\Delta = \frac{n_{1,grin}^2 - n_{2,grin}^2}{2n_{1,grin}^2} = \frac{NA_{grin}^2}{2n_{1,grin}^2} \quad (2)$$

where $NA_{grin}$ is the numerical aperture of the GRIN fiber. When a light is incident into the core of the GRIN fiber at an angle of $\theta_0$, this light will turn its direction ($\theta=0$) at the maximum radius and light equation is expressed as $$n_{1,grin}\cos(\theta_0) = n_{1,grin}\sqrt{1-2(\rho_{max}/a)^2\Delta} \quad (3)$$

In general, the radius of the light incident at an angle of $\theta$ with respect to the axial position (z) can be expressed as $$\rho(z) = \frac{a\sin(\theta)}{\sqrt{2\Delta}}\sin\left[2\pi \cdot z \Big/ \frac{2\pi a\cos(\theta)}{\sqrt{2\Delta}}\right] \quad (4)$$

where, $-\theta_0 \le \theta \le \theta_0$ describes the range of the incident angle. Clearly, Eq. (4) shows that the GRIN fiber can periodically focus the incident beam. The period is expressed as $$\Lambda = \frac{2\pi a\cos(\theta)}{\sqrt{2\Delta}} \quad (-\theta_0 \le \theta \le \theta_0) \quad (5)$$

Since the period is related to the incident angle, the self focusing effect will wash out by averaging ($-\theta_0 \le \theta \le \theta_0$) when the length of GRIN fiber is longer than $L_{max}$ as $$L_{max} = \frac{\pi \cdot n_{1,grin}}{NA_{grin}} \frac{\cos\theta_0}{1-\cos\theta_0} D_{GRIN} \quad (6)$$

For typical parameters of $D_{GRIN}$=100 µm, $\theta_0$=8°, $NA_{grin}$=0.29, $n_{1,grin}$=1.47, Eq. (6) gives $L_{max}$~160 mm. Considering a Gaussian profile power distribution with respect to the incident angle, the real maximum length is slightly longer than this value.

When $$z = \left(\frac{k}{2} + \frac{1}{4}\right)\Lambda,$$

the maximum radius is obtained from Eq. (4) as $$\rho_{max} = \frac{a\sin(\theta_0)}{\sqrt{2\Delta}} \quad (7)$$

Eq. (7) agrees with the value given by Eq. (3). Considering the fiber diameter $D_{core}$, and utilizing reflection equations for a light beam emitting from the fiber core of a single mode fiber, which is a step-index single mode fiber, in conjunction with Eq. (7), the maximum diameter $D_{max}=2\rho_{max}+D_{core}$ is then obtained as $$D_{max} = \frac{NA}{n_0\sqrt{2\Delta}}D_{grin} + D_{core} \quad (8)$$

where $D_{grin}$ is the GRIN fiber core diameter. Utilizing the reflection equations for a light beam emitting from the fiber core of a single mode fiber in conjunction with Eq. (8), the focal length of GRIN lenses without the beam expander is obtained as $$f < \left(1 - \frac{1}{e^2}\right)^2 \frac{1}{2.44\lambda}\left(\frac{NA}{n_0\sqrt{2\Delta}}D_{grin} + D_{core}\right)^2 \quad (9)$$

FIG. 7 is a table showing experimental results of the focal length for a GRIN fiber spliced onto a single mode fiber and the focal length for a fiber GRIN lens having a beam expander spliced between the GRIN fiber and a single mode fiber. For the fibers with parameters of NA=0.09, $NA_{grin}$=0.29, $n_{1,grin}$=1.487, $D_{grin}$=100,µm, the maximum beam diameter is about 40 µm when a single mode fiber is spliced onto a fiber GRIN lens. The focal length is obtained from Eq. (9) as 0.38 mm, which explains why the longest focal length is always around 0.35 mm in experiments. Experiments also show that the focal length is slightly longer for a single mode fiber with slightly larger NA, which agrees with Eq. (9). In order to obtain a long focal length, the effective way is to expand the beam diameter by splicing a short piece of beam expander (e.g., NCF or SI-MMF) between the single mode fiber and the GRIN fiber as a free space.

Figure 8:
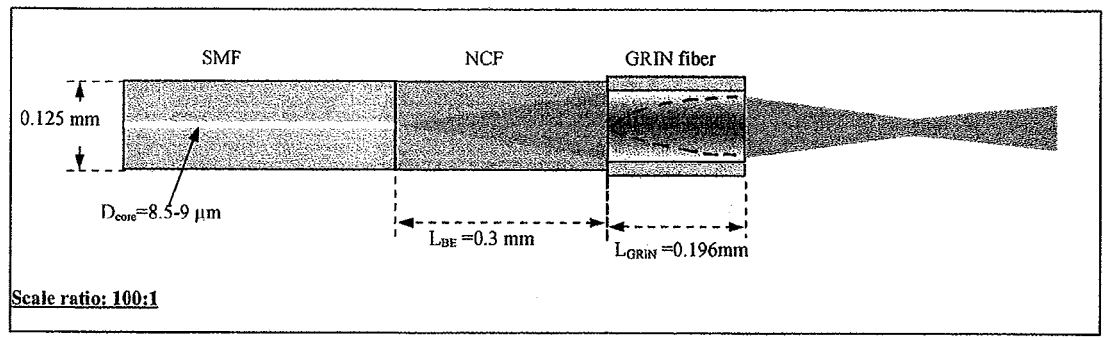
FIG. 8 is a schematic illustration of an example of a fiberoptic device in which the dimensions of a no core fiber as a beam expander and a GRIN lens that are placed at the end of an optical fiber are selected to achieve a certain long focal length.
Figure 9:
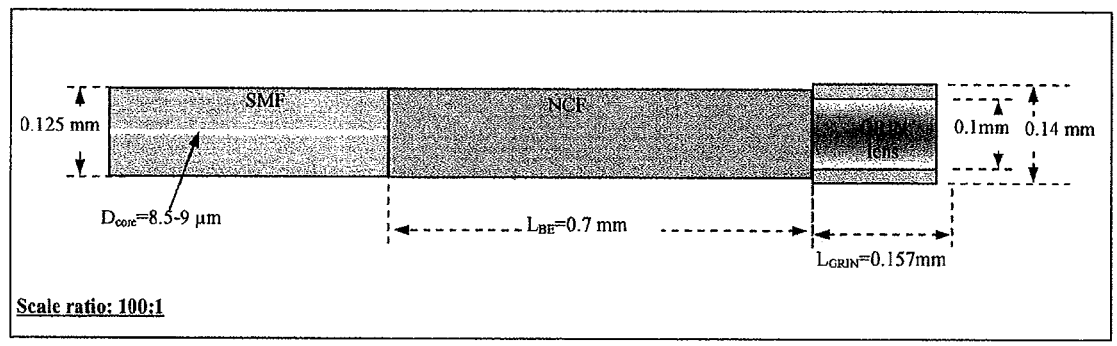
FIG. 9 is a schematic illustration of another example of a fiberoptic device in which the dimensions of a no core fiber as beam expander and a GRIN lens that are placed at the end of an optical fiber are selected to achieve a different long focal length.

FIG. 8 is a schematic illustration of an example of a fiberoptic device in which the dimensions of a no core fiber and a GRIN lens that are placed at the end of an optical fiber are selected to achieve a certain long focal length. FIG. 9 is a schematic illustration of another example of a fiberoptic device in which the dimensions of a no core fiber and a GRIN lens that are placed at the end of an optical fiber are selected to achieve a different long focal length. Note that while FIG. 9 shows a fiber GRIN lens having 0.1 mm core and 0.14 mm OD cladding, the fiber GRIN lens may have other configurations and dimensions including, for example, a 0.125 mm OD core and no cladding. In the configuration of FIG. 9, the length of the no core fiber, $L_{NCF}$, is 0.65 mm and the length of the GRIN fiber is 0.17 mm. This produces the experimental result of a long focal length equal to 1.76 mm. In the configuration of FIG. 8, the length of the no core fiber is 0.3 mm instead of 0.65 mm, while the length of the GRIN fiber is 0.26 mm instead of 0.17 mm. The measured focal length for the configuration of FIG. 8 is 0.62 mm, which is smaller than the focal length of 1.76 mm for the configuration of FIG. 9 because the beam diameter is smaller for the shorter no core fiber in FIG. 8. When the length of the no core fiber and the diameters of the GRIN fiber and the no core fiber are doubled, the theoretical focal length would be increased by four times, which could be a few millimeters long. For large dimension fibers, a special designed fusion splicer rather than the regular one may have to be used. Additional details of the SMF, NCF, and GRIN lens can be found in U.S. patent application Ser. No. 12/829,787, filed Jul. 2, 2010, which is incorporated herein by reference in its entirety.

In the description, numerous details are set forth for purposes of explanation in order to provide a thorough understanding of the present invention. However, it will be apparent to one skilled in the art that not all of these specific details are required in order to practice the present invention. Additionally, while specific embodiments have been illustrated and described in this specification, those of ordinary skill in the art appreciate that any arrangement that is calculated to achieve the same purpose may be substituted for the specific embodiments disclosed. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. A method of forming an optical coherence tomography (OCT) rotation catheter, the method comprising:
   placing a tubular member in a catheter body, the tubular member having a hollow interior extending between a proximal end and a distal end, a longitudinal axis extending in a longitudinal direction between the distal end and the proximal end, the tubular member being rotatable around the longitudinal axis;
   providing an optical fiber extending along the hollow interior of the tubular member and having an optical fiber distal end at a location near the distal end of the tubular member to direct light through the optical fiber distal end toward the distal end of the tubular member;
   forming a light reflecting member which is a longitudinal member and has a diameter of at most about 0.25 mm; and
   positioning the light reflecting member in the hollow interior of the tubular member along the longitudinal axis and distal of the optical fiber distal end, wherein the light reflecting member is configured to rotate around the longitudinal axis with the tubular member, the light reflecting member including a light reflecting end surface which is spaced from and faces the optical fiber distal end, wherein the light reflecting end surface inclined to reflect the light from the optical fiber in a radial direction at an angle with respect to the longitudinal axis, the reflected light rotating in a circumferential direction due to rotation of the light reflecting member around the longitudinal axis;
   wherein forming the light reflecting member comprises forming a bundle of at least five longitudinal members having end surfaces exposed at an end of the bundle; polishing collectively the exposed end surfaces of the longitudinal members at the end of the bundle; coating the polished end surfaces of the longitudinal members with a light reflecting film; and separating the bundle to provide each longitudinal member as a light reflecting member having the coated end surface as a light reflecting end surface; and
   wherein the longitudinal members are metal wires.

2. The method of claim 1,
   wherein the tubular member and the catheter are optically transparent at least in a region near the light reflecting member to allow the reflected light from the light reflecting end surface to pass therethrough.

3. The method of claim 1, further comprising:
   coupling a first end of a beam expander to the distal end of the optical fiber, the beam expander having a second end, the beam expander permitting a light beam emitting from a fiber core of the optical fiber to pass from the first end to the second end and to expand from the first end to a larger beam size at the second end; and
   coupling a gradient-index fiber lens to the second end of the beam expander to receive the light beam from the beam expander and focus the light beam;
   wherein the gradient-index fiber lens is proximal of the light reflecting member and spaced from the light reflecting end surface.

4. The method of claim 3,
   wherein the optical fiber is a single mode fiber; and
   wherein the beam expander comprises a no core fiber or a step-index multimode fiber.

5. The method of claim 3,
   wherein the gradient-index fiber lens has a core surrounded by a glass cladding or air, the core having a refractive index that varies with a radial distance from an axis of the gradient-index fiber lens, decreasing radially outwardly toward the cladding; and
   wherein the core of the gradient-index fiber lens has a diameter which is not smaller than an outer diameter of the beam expander.

6. The method of claim 3,
   wherein the gradient-index fiber lens has a refractive index that varies with a radial distance from an axis of the gradient-index fiber lens, decreasing radially outwardly; and
   wherein the gradient-index fiber lens has a diameter which is not smaller than an outer diameter of the beam expander.

7. The method of claim 1,
   wherein the stationary shaft tubular member is optically transparent at least in a region near the light reflecting member to allow the reflected light from the light reflecting end surface to pass therethrough.

8. The method of claim 1,
   wherein the tubular member is rotatable with respect to the catheter body; and
   further comprising providing a clearance of less than about 0.25 mm between an outer surface of the tubular member and an inner surface of the catheter body.

9. The method of claim 1, further comprising:
   attaching the light reflecting member and the optical fiber distal end to the tubular member to rotate with the tubular member around the longitudinal axis with respect to the catheter body; and
   sealing a distal end of the catheter body which is distal of the distal end of the tubular member.

10. The method of claim 1,
    wherein the longitudinal members are stainless steel wires.

11. The method of claim 1,
wherein the light reflecting film comprises a material selected from the group consisting of aluminum, silver, gold, and dielectric coating materials.

12. The method of claim 1,
wherein the bundle has at least a 100 longitudinal members.

13. The method of claim 1,
wherein the exposed end surfaces of the longitudinal members at the end of the bundle are collectively polished at an angle to a longitudinal axis of the bundle.

14. The method of claim 1,
wherein the exposed end surfaces of the longitudinal members at the end of the bundle are collectively polished at an angle to a longitudinal axis of the bundle to form an inclined plane with the polished end surfaces.

* * * * *